Figure 1A:
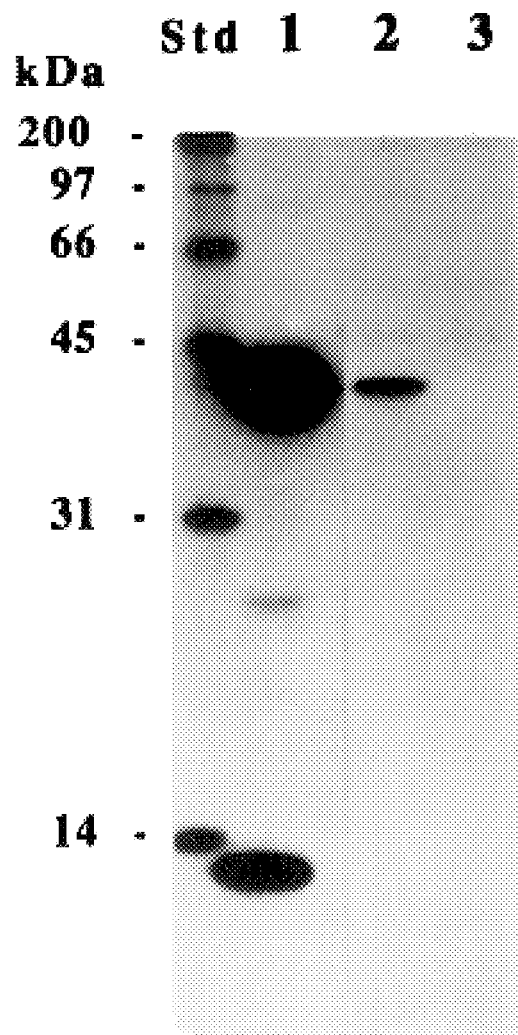

US006150123A

United States Patent
Cosma

[11] Patent Number: 6,150,123
[45] Date of Patent: Nov. 21, 2000

[54] AFFINITY BIOTINYLATION

[75] Inventor: Antonio Cosma, Paris, France

[73] Assignee: Centre Integre de Recherches Biocliniques sur le Sida (CIRBS)

[21] Appl. No.: 09/146,587

[22] Filed: Sep. 3, 1998

[51] Int. Cl.[7] .................. G01N 33/53; G01N 33/573; G01N 33/531; A23J 1/00
[52] U.S. Cl. .................. 435/7.5; 435/7.4; 435/7.7; 435/7.72; 435/7.8; 435/7.92; 435/7.93; 435/7.94; 435/7.95; 435/969; 435/970; 436/501; 436/526; 436/529; 436/530; 436/531; 436/534; 436/544; 436/827; 530/413
[58] Field of Search .................. 435/7.5, 7.4, 7.7, 435/7.72, 7.8, 7.92–7.95, 969, 970; 436/501, 526, 529, 530, 531, 534, 544, 827; 530/413

[56] References Cited

U.S. PATENT DOCUMENTS

| | | | |
|---|---|---|---|
| 4,251,360 | 2/1981 | Goldie et al. | 424/1.5 |
| 4,279,885 | 7/1981 | Reese et al. | 424/1 |
| 4,371,515 | 2/1983 | Chu | 436/544 |
| 4,447,526 | 5/1984 | Rupchock et al. | 435/7 |
| 4,504,585 | 3/1985 | Reynolds | 436/518 |
| 4,506,009 | 3/1985 | Lenhoff et al. | 435/7 |
| 4,629,688 | 12/1986 | Bolguslaski et al. | 436/537 |
| 4,791,066 | 12/1988 | Ishiguro | 436/514 |
| 5,256,532 | 10/1993 | Melnicoff et al. | 435/5 |
| 5,320,968 | 6/1994 | Seman | 436/7.1 |
| 5,462,853 | 10/1995 | Steward et al. | 435/5 |
| 5,580,742 | 12/1996 | Bodenmuller et al. | 435/7.94 |
| 5,773,222 | 7/1998 | Scott | 435/7.1 |
| 5,789,165 | 8/1998 | Oku et al. | 435/6 |
| 5,830,709 | 11/1998 | Benson et al. | 435/7.92 |

OTHER PUBLICATIONS

Doyle et al. "Applications of Lectins in Microbiology" ASM News. vol. 55 No. 12 (1989) pp. 655–658.
Wang et al."A Colorimetric Method for Detection of Specific Ligand Binding" Analytical Biochemistry 204, (1992) pp. 59–64.
Hayman et al. "Purification of Virus Glycoproteins by Affinity Chromatography Using *Lens culinaris* PHytohaemagglutinin" FEBS Letters. vol. 29 No. 2 (Jan. 1973) pp. 185–188.
Avellana–Adalid et al. "Biotinylated Derivative of a Human Brain Lectin" Analytical Biochemistry 190 (1990) pp. 26–31.
Cosma, (Oct.) 1997, Analytical Biochemistry 252:10–14.
Altin and Pagler, 1995, Analytical Biochemistry 224:382–389.
Altin et al., 1994, Immunology 83:420–429.
Meier et al., 1992, Analytical Biochemistry 204:220–226.
Nesbitt and Horton, 1992, Analytical Biochemistry 206:267–272.

*Primary Examiner*—Christopher L. Chin
*Assistant Examiner*—Pensee T. Do
*Attorney, Agent, or Firm*—BakerBotts, NY

[57] ABSTRACT

The present invention relates to a method for biotinylating a desired subset of a larger population of proteins, wherein the subset of proteins is first selectively bound to a solid phase, thereby separating it from undesired proteins of the population, and then, still bound to solid phase, it is biotinylated. Unreacted biotin may then be washed from the solid phase, and the biotinylated protein may be uncoupled from the solid phase.

12 Claims, 3 Drawing Sheets

AFFINITY BIOTINYLATION

1. INTRODUCTION

The present invention relates to a method for detectably labeling with biotin ("biotinylating") a subset of a larger population of proteins wherein, prior to the biotinylation step, the subset of proteins is selected from the population of proteins by affinity binding to a solid phase. The method of the invention has been found to be faster and more practical than conventional methods of labeling with radioisotope, without any loss in sensitivity.

2. BACKGROUND OF THE INVENTION

Conventional methods for the detection and characterization of cell surface antigens involve surface radiolabeling with $^{125}$I(Morrison, 1980, Methods Enzymol. 70:214–220), whereas analysis of the total cellular protein pool is usually achieved by metabolic radiolabeling with [$^{35}$S]methionine and [$^{35}$S]cysteine(Coligan et al., 1983, Methods Enzymol. 91:413–434). Biotin is a powerful, nonradioactive reagent for labeling proteins and has been used to successfully label cell surface proteins on intact (Meier et al., 1992, Anal. Biochem. 204:220–226; Nesbitt and Horton, 1992, Anal. Biochem. 206:267–272) and permeabilized (Altin and Paglet, 1995, Anal. Biochem. 224:382–389; Altin et al., 1994, Immunol. 83:420–429) cells, but, being unsuitable for metabolic labeling, has not been considered an adequate alternative to radioisotopes for labeling intracellular proteins.

3. SUMMARY OF THE INVENTION

The present invention relates to a method in which biotin is used to label a subset of proteins, not limited to cell surface proteins, of a larger protein population, such as the total cellular protein pool. The subset of proteins is first separated from undesired proteins by selective binding to a solid phase, and then, still bound to the solid phase, is biotinylated.

The method of the invention offers several advantages over either conventional biotinylation or radiolabeling methods. It eliminates many of the drawbacks of radioactive isotopic protein, including laboratory safety concerns, containment and disposal costs, and limited half-life of radioactive isotopes. Unlike conventional use of biotin, it permits the efficient labeling of non-cell surface proteins.

Relative to the alternative of biotinylating a population of solubilized proteins and subsequently isolating a subset of proteins of interest, the present invention permits greater specificity in protein labeling, for several reasons. First, if a soluble population of proteins is biotinylated, removal of unreacted biotin is problematic. In contrast, in the method of the invention, unreacted biotin may be removed by washing from the solid phase. Second, where a soluble population of proteins has been biotinylated, and then separation of a subset of protein is attempted by immunoprecipitation, nonspecific binding results in co-precipitation of undesired biotinylated protein. Where a specific set of proteins has been preselected prior to labeling, this second problem is virtually eliminated. Further, where retention and release of protein on the solid phase is mediated by a particular ligand, there is an additional safeguard against inclusion of undesired protein, as a protein nonspecifically retained on the solid phase is unlikely to be eluted by ligand.

4. DESCRIPTION OF THE FIGURES

Figure 1B:
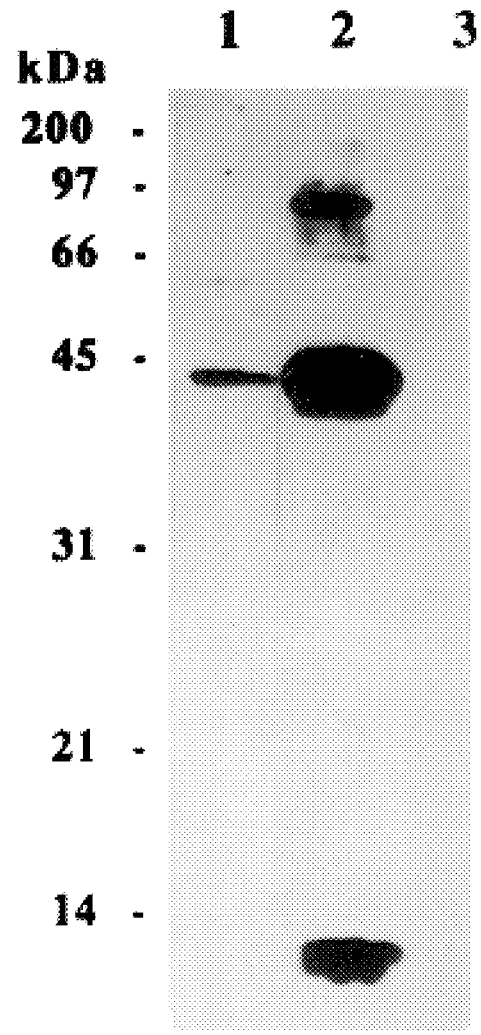

FIGS. 1A–B. SDS-PAGE analysis of immunoprecipitates from metabolically labeled and affinity biotinylated LG2 cell line. In [A], the LG2 cell line was radiolabeled with [$^{35}$S] methionine and [$^{35}$S]cysteine and lysed in one percent NP-40. Immunoprecipitation was performed with mAb W6/32 (lane 1), L31 (lane 2) and a control mAb (lane 3). The first lane corresponds to the protein standards. The immunoprecipitates were resolved by SDS-PAGE (12% gel) under reducing conditions and the dried gel was autoradiographically exposed for 1 week. In [B], glycoproteins from the LG2 lysate were affinity selected on Lens lectin-Sepaharose 4B, biotinylated, and then eluted with the counterligand buffer containing 1 M methyl α-D-mannopyranoside. Eluted glycoproteins were immunoprecipitated with mAb L31 (lane 1), W6/32 (lane 2), and a control mAb (lane 3). The immunoprecipiates were resolved by SDS-PAGE, blotted onto a nitrocellulose membrane, and probed with avidin-HRP.

Figure 2:
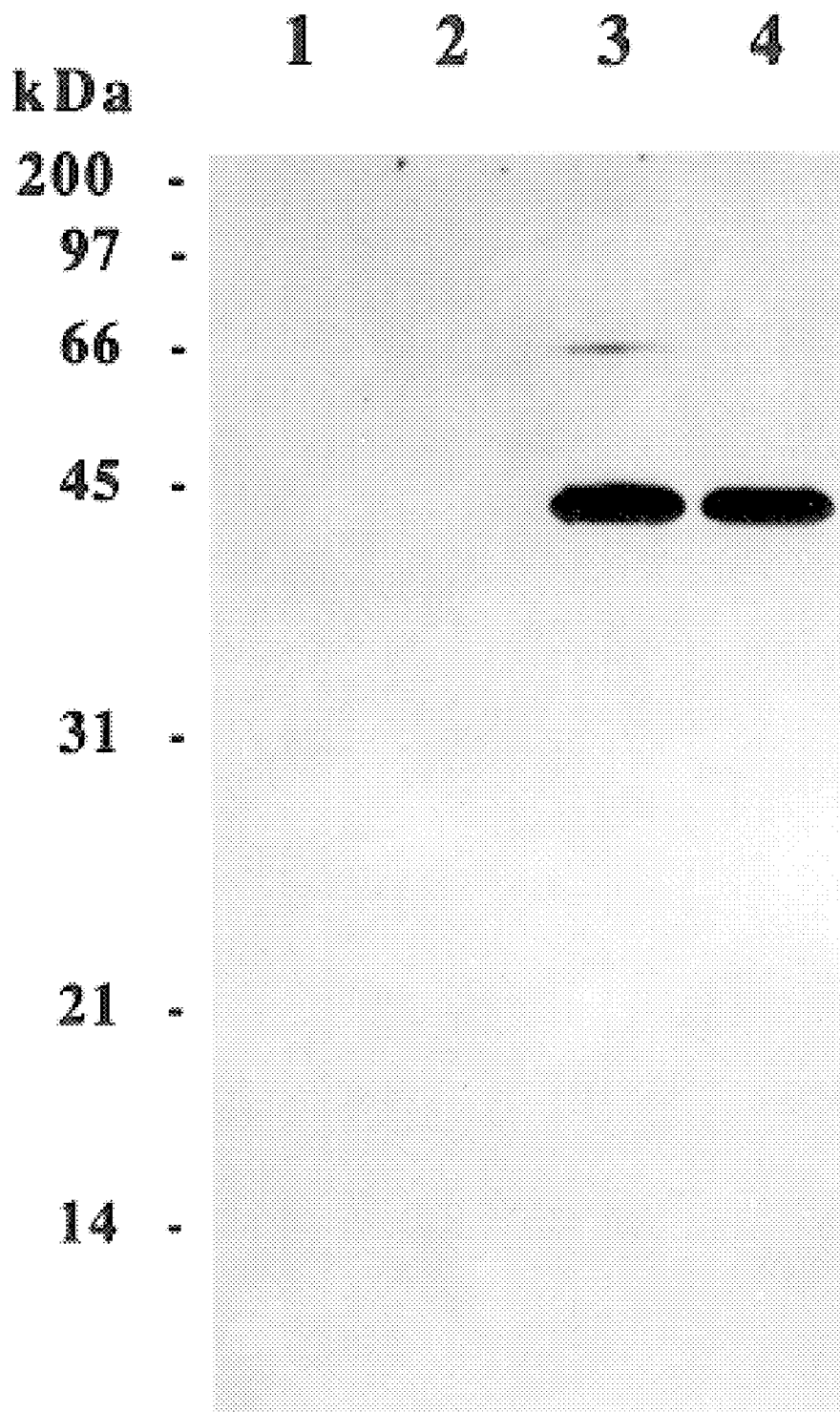

FIG. 2. SDS-PAGE analysis of immunoprecipitates from affinity biotinylated lysate of 221- and 221 Cw4-transfected cell lines. Soluble NP-40 extract from 221 and 221 Cw4-transfected ("221 Cw4") cell lines were adsorbed to Lens lectin-Sepharose 4B, biotinylated, and eluted. Eluted glycoproteins from 221 (lanes 1 and 2) and 221 Cw4 (lanes 3 and 4) cell lines were immunoprecipitated with L31 mAb (lanes 1 and 3) and W6/32 mAb (lanes 2 and 4). The immunoprecipitates were analyzed by SDS-PAGE (12% gel). The 12-kDa $\beta_2$m band (lane 4) barely detectable in the original film is not visible in the photo.

Figures 3A, 3B:
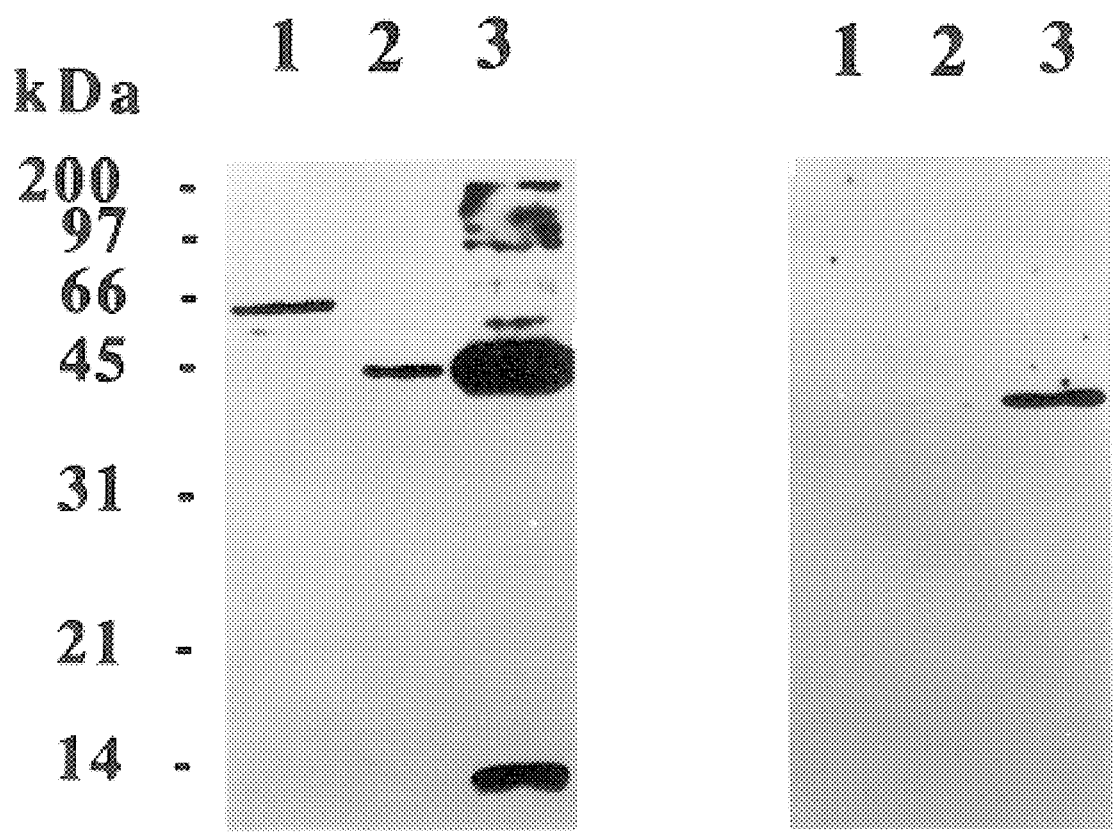

FIG. 3A–B. SDS-PAGE analysis of immunoprecipitates from affinity-biotinylated LG2 lysate and from nonbiotinylated LG2 lysate probed with mAb L31. In [A] the LG2 lysate was adsorbed to Lens lectin-Sepharose 4B, biotinylated, and eluted. In a parallel experiment [B], LG2 lysate was adsorbed to Lens lectin-Sepharose 4B and eluted. Biotinylated and nonbiotinylated glycoproteins were immunoprecipitated with a control mAb (lanes 1), L31 mAb (lanes 2), and BBM.1 mAb (lanes 3). The immunoprecipitates were analyzed by SDS-PAGE (12% gel), transferrred to nitrocellulose, and probed with avidin-HRP [A] or L31 mAb followed by rabbit anti-mouse-HRP [B].

5. DETAILED DESCRIPTION OF THE INVENTION

The present invention relates to a method for detectably labeling with biotin a subset of a larger population of proteins comprising first (i) contacting the larger population of proteins with an affinity element, attached to a solid phase element, which selectively binds to the subset of proteins, under conditions which permit binding of the affinity element to the subset of proteins to occur; (ii) removing protein not bound to the solid phase element; and (iii) linking biotin to ("biotinylating") the subset of proteins bound to the solid phase element.

The affinity element selectively binds to the subset of proteins of interest via a ligand-ligand partner interaction. The affinity element may, for example, comprise an antibody or a fragment thereof which specifically binds to a target antigen comprised in the subset of proteins of interest. Alternatively, and as exemplified in the nonlimiting working example provided herein, the affinity element may comprise a lectin, which selectively binds to glycoprotein comprised in a subset of proteins of interest. In further nonlimiting embodiments, the affinity element may comprise a ligand which binds to a particular cellular receptor, or a subunit of a multimeric protein which selectively binds to one or more components of the multimeric protein, or a cofactor or substrate of a subset of proteins of interest. For example, where the subset of proteins of interest consists of one or more enzyme, a substrate or a cofactor for such enzyme may be used as the affinity element.

The affinity element may further comprise a chemical structure which facilitates its coupling to a solid phase element and/or its accessibility for binding to its target protein.

Suitable solid phase elements include, but are not limited to, arylamide derivatives, methacrylate derivatives, polystyrene and polystyrene derivatives, magnetic beads, agarose and Sepharose™ 4B. The affinity element may be coupled to the solid phase element by any method known in the art. Where the affinity element is an antibody, the antibody may be bound to the resin by, for example, but not limited to, a cyanogen bromide activation method, as is described in "Short Protocols in Molecular Biology", 1995, Ausubel et al., eds., John Wiley & Sons, Inc., New York, pp. 10-72–10-73. Affinity element attached to a solid phase element may also be purchased from a commercial manufacturer.

The larger population of proteins from which the desired subset is selected may be any collection of proteins, including, but not limited to, total cellular protein, intracellular proteins, nuclear proteins, or any subpopulation thereof, or may be proteins secreted from a cell or expressed by an expression library.

The subset of proteins may contain one or more than one species of protein.

The initial binding of the subset of proteins to an affinity element comprised in a solid phase may be performed under conditions which may vary depending upon the nature of the ligand-ligand partner interaction. For example, where the affinity element is a lectin, the subset of proteins (glycoproteins) may be bound by incubating a larger population of proteins with lectin bound to a solid phase element in a binding buffer which is 0.25% NP-40 in PBS for about 3 hours at 4° C., with rotation. Where the affinity element is an antibody, a method such as that described in "Short Protocols in Molecular Biology", 1995, Ausubel et al., eds., John Wiley & Sons, Inc., New York, pp. 10-55–10-58 may be used. After binding, the solid phase may be washed with an effective volume of a solution (for example, a volume at least 5–10 times the volume of solid phase), to remove unbound sample components.

Biotinylation may be performed for example, but not limited to, by reaction with NHS-biotin, at a concentration of about 3.2 percent (v/v), for 30 minutes at 4° C., or using any method known in the art, for example, as set forth in Meier et al., 1992, Anal. Biochem. 204:220–226; and Nesbitt and Horton, 1992, Anal. Biochem. 206:267–272.

Following biotinylation, unreacted biotin may be removed by washing the solid phase, and its retained protein, with an effective volume of a solution (generally at least 10–20 times the volume of the solid phase).

Biotinylated protein may then be selectively eluted from the affinity column by ligand or a competitive inhibitor of the ligand-ligand partner interaction, or, less preferably, may be nonselectively eluted by altering conditions (e.g., ionic strength, pH) to disfavor the ligand-ligand partner interaction. For example, where glycoprotein has been bound to the solid phase via a lectin, the biotinylated glycoproteins may be selectively eluted using the competitive inhibitor methyl α-D-mannopyranoside (1 M) in 0.25% NP-40 in PBS, for 2 hours, at 4° C., with rotation.

A nonlimiting example of the foregoing method is set forth in Section 6, below. A smaller scale version is set forth in Section 7. In another specific nonlimiting embodiment of the invention, the affinity element may be an antibody, preferably a monoclonal antibody, which has, as its target antigen, phosphotyrosine ("anti-PT Ab"), coupled to agarose. The anti-PT Ab-agarose solid phase may then be used to select, from a larger population of proteins, the subset of phosphotyrosine-containing proteins, which may then be biotinylated with NHS-biotin. The biotin-labeled phosphotyrosine-containing proteins may then be eluted from the solid phase with phenyl phosphate.

6. EXAMPLE: AFFINITY BIOTINYLATION OF GLYCOPROTEINS

6.1. MATERIALS AND METHODS

Reagents. Biotin-spacer arm -N-hydroxysuccimide ester in di-methylformamide was obtained from Amersham (Little Chalfont, UK). Lectin from Lens culinaris coupled to Sepharose 4B beads (Seph-LcH) and methyl α-D-mannopyranoside were obtained from Sigma (St. Louis, Mo.). The mAbs used were as follows: mouse monoclonal antibody ("mAb") W6/32, which has as its target antigen a determinant carried by all class I heavy chains (Brodsky et al., 1979, Immunol. Rev. 47:3), including $\beta_2$m-associated HLA-C (Hajek-Rosenmayer et al., 1989, Immunogenetics 29:323, Mizuno et al., 1989, Immunogenetics 29:323); mAb L31, which has, as its target antigen, a determinant carried by all HLA-C $\beta_2$m-free heavy chains (Setini et al., 1996, Human Immunol. 46:69–81); mAb BBM.1, which has, as its target antigen, free and HLA-A and -B-associated human $\beta_2$m with similar affinity (Parham et al., 1983, J. Biol. Chem. 258:6179–6186).

Cell lines. LCL 721.221 is a human B-lymphoblastoid cell line that does not express endogenous HLA-A, -B, or -C due to a γ-ray-induced mutation in the HLA complex (Shimizu and DeMars, 1989, J. Immunol. 46:69–81). LCL 721.221 and LCL 721.221-transfected with the HLA allele Cw4 were gifts of R. Biassoni. LG2 is an HLA homozygous (HLA-A2, B27, C1), EBV-transformed continuous B cell line and was provided by P. Giacomini.

Metabolic Radiolabeling and Cell Lysis. Cells were radiolabeled as described in Catipovic, et al., 1992, J. Exp. Med. 176:1611–1618, with 100 μCi/ml of [$^{35}$S]cysteine (ProMix; Amersham). Cells ($10^7$) were lysed on ice in 200 μl lysis buffer (1% Nonidet P-40 ("NP-40"), 1 mM phenylmethylsulfonyl fluoride, 2 μg/ml aprotinin in PBS). After a 30 minute incubation on ice, the nuclei were sedimented at 14,000 rpm for 5 minutes at 4° C.

Lectin Adsorption, Biotinylation and Elution. Cell lysate glycoproteins were adsorbed to the solid phase by incubating 200 μl cell lysate with 75 μl Seph-LcH in 150 μl of 0.25% NP-40 in PBS ("PBS-NP"), for 3 hours at 4° C., with rotation. The resulting Seph-LcH-glycoprotein complex was washed with at least 10 bed volumes PBS-NP to remove unbound sample components, and then resuspended 1:4 with the same buffer before addition of NHS-biotin (3.2% v/v). The Seph-LcH-glycoprotein complex was then incubated with NHS-biotin for 30 minutes at 4° C. with gentle rotation, and then successively washed with 20 bed volumes of PBS-NP to remove unreacted biotin. The glycoproteins were eluted from the Seph-LcH by incubation with 400 μl of PBS-NP buffer containing the competitive inhibitor methyl α-D-mannopyranoside (1 M) for 2 hours at 4° C. with rotation.

Immunoprecipitation. MAbs coupled to CNBr-activated Sepharose 4B (Pharmacia, Uppsala, Sweden) (Seph-mAb, 10 μg mAb/μl sepharose gel) were incubated with radiolabeled or biotinylated lysate as follows. Radiolabeled lysate was incubated with 10 μl Seph-mAb in 50 mM Tris, 150 mM NaCl, 5 mM EDTA, 0.03% NaN$_3$, 0.25% NP-40, 10% FCS, pH 7.4 for 2 hours at 4° C. with rotation. Biotinylated lysate was incubated under the same conditions, using PBS-NP with 1 M methyl-α-D-mannopyranoside for the incubation buffer. The Seph-mAb immunoprecipitates were then washed at 4° C. seven times with 50 mM Tris, 150 mM NaCl, 5 mM EDTA, 0.03% NaN$_3$, 0.25% NP40, 0.1% BSA, pH 7.4 and three times with the same buffer without BSA. The Seph-mAb immunoprecipitates were resuspended in 95 μl nonreducing SDS-PAGE sample buffer (Laemmli, 1970, Nature 227:680–685) and after 15 minutes the suspension was centrifuged in a Spin-X centrifuge tube filter (Costar, U.S.A.), retaining the liquid phase containing the precipitated material. Then, 5 μl of 14.2 M β-mercaptoethanol was added to the precipitated material.

Electrophoresis, Western Blotting, and Protein Detection by Enhanced Chemiluminescence. Samples were resolved on a one-dimensional SDS-polyacrylamide slab gel using the method of Laemmli (1970, Nature 227:680–685). After SDS-PAGE, the proteins were transferred electrophoretically to a nitrocellulose membrane (BIORAD, Richmond, Calif.). Biotinylated glycoproteins were detected by incubation with acetyl-avidin horseradish peroxidase complex (SPA, Milan, Italy). Alternatively, non-biotinylated proteins were probed first with a primary mAb (L31) and then with rabbit anti mouse-HRP complex (DAKO, Glostrup, Denmark), diluted respectively 1/50 and 1/1000. The membranes were then developed using an enhanced chemiluminescence system (ECL, Amersham, Little Chalfont, U.K.).

Autoradiography. The gel was fluorographed using Amplify (Amersham, Little Chalfont, U.K.) and dried under vacuum at 70$_t$C. Autoradiography of the dried gel was performed at –80$_t$C using Amersham Hyperfilm-MP.

6.2. RESULTS

Comparison of affinity biotinylation and metabolic radio-labeling of proteins from total cellular lysate. LG2 cells were metabolically labeled with [$^{35}$S]methionine and [$^{35}$S]cysteine, solubilized by nonionic detergent (NP-40) and immunoprecipitated with the mAbs W6/32 and L31, specific for the HLA class I heavy chain associated with β$_2$m and the free heavy chain, respectively. Immunoprecipitated molecules were resolved by SDS-PAGE and detected by autoradiography of the dried gel (FIG. 1A). Alternatively LG2 NP-40- solubilized lysate was affinity bound to Lens lectin-Sepharose 4B, biotinylated, eluted and immunoprecipitated with mAb W6/32 and L31. Immunoprecipitated molecules, resolved by SDS-PAGE, were blotted onto a nitrocellulose membrane and detected with avidin-HRP (FIG. 1B). The specific detection of metabolically labeled heavy chain and β$_2$m precipitated with mAb W6/32 (FIG. 1A, lane 1) was qualitatively similar to that obtained with biotinylated glycoproteins (FIG. 1B, lane 2). The biotinylation technique gave improved resolution, and in addition to the major heavy chain and β$_2$m components, one additional band of 80–100 kDa was visible. Free heavy chain immunoprecipitated with mAb L31 from metabolically labeled lysate or biotinylated lysate produced identical results (FIG. 1A, lane 2 and FIG. 1B, lane 1). Overall, the affinity biotinylated glycoproteins produced strong signals with low background.

Immunoprecipitation of Cw4 allele from a transfected cell line. To assess the specificity of the affinity biotinylation technique, biotinylated lysates of human B-lymphoblastoid cells (LCL 721.221) transfected with HLA Cw4 allele, as well as non transfected LCL 721.221 cells, were immunoprecipitated with mAb W6/32 and L31 (FIG. 2). As expected, no signals were detected in immunoprecipitates from non transfected cells (FIG. 2, lane 1 and 2) and background was not detectable after 30' of exposure. In the Cw4 transfected cells, mAb W6/32 precipitated the heavy chain with the expected 44 kDa molecular weight, while the 12 kDa β$_2$m polypeptide was barely detectable, in agreement with the known weak association of HLA-C heavy chain with β$_2$m (Neefjes and Ploegh, 1988, Eur. J. Immunol. 18:801–810) (FIG. 2, lane 4). As expected, mAb L31 precipitated only the Cw4 free heavy chain (FIG. 2, lane 3).

Sensitivity of affinity biotinylation procedure compared to standard western blot detection of immunoprecipitated lectin-selected proteins. The affinity biotinylation procedure, in which lectin selected proteins are biotinylated before immunoprecipitation and then detected with avidin-HRP after nitrocellulose transfer, was compared to another non radioactive procedure in which immunoprecipated lectin selected proteins are detected by a Western blot procedure using biotinylated mAb L31 as the antibody probe, followed by avidin-HRP. LG2 NP40 solubilized lysates were affinity bound to lens lectin-Sepharose 4B, divided into two aliquots, one of which was biotinylated (lysate-B) and the other left untreated (lysate-U). Both were eluted and separately immunoprecipitated with mAb L31 and mAb BBM.1. The lysate-U samples were resolved by SDS-PAGE, blotted onto a nitrocellulose membrane and probed with mAb L31. The lysate-13 samples were resolved by SDS-PAGE, blotted onto a nitrocellulose filter, and probed with avidin-HRP (FIG. 3). As expected, in the lysate-B samples, mAb BB.M1 immunoprecipitated the β$_2$m and its associated HLA class I heavy chain (FIG. 3A, lane 3) whereas L31, as shown before (FIG. 1B, lane 1) recognised only the free heavy chain (FIG. 3A, lane 2). FIG. 3B shows the results from lysate-U probed with mAb L31, which recognizes denatured heavy chain polypeptides. Here, as expected, mAb L31 recognised the heavy chains precipitated by mAb BB.M1 (FIG. 3B, lane 3) and L31 (FIG. 3B lane 2). The bands produced by heavy chains immunoprecipated from lysate-B (FIG. 3A, lane 2 and 3) were more intense than those of heavy chains from lysate-U (FIG. 3B, lane 2 and 3). The exposure time of nitrocellulose filters was identical in both experiments. A slight shift was evident in apparent molecular weight between immunoprecipitates from lysate-B (biotinylated proteins) and lysate-U.

6.3 DISCUSSSION

The present invention relates to a non radioactive technique for the biochemical characterization of intracellular and plasma membrane proteins. This method is based on the innovative step of biotinylation of glycoproteins affinity bound to lectin. The biotinylated glycoproteins can then be eluted and used in immunoprecipitation.

Plant lectins are carbohydrate binding proteins with a variety of specificities, and have proven especially useful for characterization of glycoconjugates. Lens culinaris lectin (LcH) specifically binds α-D-glucose and α-D-mannose residues (Martin et al., 1971, J. Biol. Chem. 246:1596–1601) and retains its binding capacity in the presence of non-ionic detergents (Hayman et al., 1973, FEBS Lett. 29:185–188). Therefore, LcH-Sepharose 4B was chosen for our protocol to affinity select detergent solubilized cellular glycoproteins to be labeled with biotin.

Biotinylation of an affinity selected pool of proteins may be considered preferable to direct biotinylation of a cell lysate since the unreacted biotin can be readily removed from the solid matrix simply by washing. The affinity step allows selection of specified proteins in the lysate, thereby narrowing the pool of target proteins at an early stage in the procedure. The affinity purification step functions as a preclearing passage because the elution is achieved by competition with methyl-α-D-mannopyranoside, so molecules bound non-specifically to the resin are not eluted.

The present work shows that the affinity biotinylation procedure is a valid alternative to metabolic radiolabeling of glycoproteins. Biotinylation does not depend on biosynthesis, therefore all of the proteins are labeled, even those normally synthesized at a slow rate. Our results from applying affinity biotinylation prior to immunoprecipitation illustrate the potential for detecting proteins not otherwise labeled by standard radioimmunoprecipitation. Indeed, in addition to the expected band of 44 kDa corresponding to the HLA heavy chain, immunoprecipitation of biotinylated LG2 cell lysate with mAb W6/32 (FIG. 1B, lane 2) yielded another band of 80–100 kDa that was not detected by radioimmunoprecipitation of the non-biotinylated lysate. The additional band may represent the associated chaperone protein which can coprecipitate with the heavy chain $\beta_2$m heterodimer (Carreno et al., 1995, J. Immunol. 155:4726–4733).

The affinity biotinylation procedure is both sensitive and specific. Sensitivity was superior to a standard western blot and probing procedure using mAb L31, producing bands of higher intensity with the same exposure time and mAb concentration, as shown in FIG. 3. A slight shift in apparent molecular weight between the biotinylated proteins and the non biotinylated proteins detected with mAb L31 was noted (FIG. 3). This is a common artifact resulting from the high biotin-protein ratio in the biotinylation reaction, and does not affect the overall interpretation of the result. Specificity was tested by comparing monoclonal antibody immunoprecipitation of non HLA expressing cells with the same cells transfected with HLA CW4. As shown in FIG. 2, no bands were evident in the non-transfected cell immunoprecipitates, and the background reactivity was also very low.

There are other beneficial features of the affinity biotinylation procedure. It allows for detection of non glycosylated proteins that are associated with the glycoproteins affinity absorbed to the solid matrix. This can be seen in FIG. 1B, lane 2 and in FIG. 3A, lane 3 where the non glycosylated protein $\beta_2$m, associated with the HLA heavy chain, gave a strong signal. Thus, the technique may be suitable for labeling complexes of proteins. By varying the affinity ligand, it is possible to select different classes of molecules or even a single protein of interest.

In summary, the present invention provides for a practical and efficient non-radioactive method for labeling a homogeneous pool of cellular proteins. The results are equivalent or superior to standard radiometabolic labeling. This technique can be applicable to a wide range of studies merely by substituting the ligand in the affinity step.

7. EXAMPLE: SMALL SCALE AFFINITY BIOTINYLATION

Cell Lysis. Cells ($10^6$) were lysed on ice in 20 µl lysis buffer (1% Nonidet P-40, 1 mM phenylmethylsulfonyl fluoride, 2 µg/ml Aprotinin in PBS). After 30 minutes of incubation on ice, the nuclei were sedimented at 14,000 rpm for 5 minutes at 4° C.

Lectin Adsorption, Biotinylation and Elution. Cell lysate glycoproteins were adsorbed to the solid phase by incubating 20 µl cell lysate with 7.5 µl Seph-LcH in 15 µl of 0.25% NP40 in PBS (PBS-NP), for 3 hours at 4° C., with rotation. The Seph-LcH-glycoprotein complex was washed with at least ten bed volumes PBS-NP to remove unbound sample components, and then resuspended 1:4 with the same buffer before addition of NHS-biotin (3.2% vol/vol). The Seph-LcH-glycoprotein complex was then incubated with NHS-biotin for 30 minutes at 4° C. with gentle rotation and successively washed with twenty bed volumes of PBS-NP to remove unreacted biotin. The glycoproteins were eluted from the Seph-LcH by incubation with 100 µl of PBS-NP buffer containing the competitive inhibitor methyl-α-D-mannopyranoside (1 M) for 2 hours at 4° C. with rotation.

Immunoprecipitation. MAbs coupled to CNBr-activated Sepharose 4B (Pharmacia, Uppsala, Sweden) 10 µg mAb in 10 µl of resin, were incubated with biotinylated lysate. Biotinylated lysate was incubated for 2 hours or overnight at 4° C. with rotation, using PBS-NP with 1 M methyl-α-D-mannopyranoside for the incubation buffer. The Seph-mAb immunoprecipitates were then washed at 4° C. seven times with 50 mM Tris, 150 mM NaCl, 5 mM EDTA, 0.03% $NaN_3$, 0.25% NP40, 0.1% BSA, pH 7.4 and three times with the same buffer without BSA. The Seph-mAb immunoprecipitates were resuspended in 28.5 µl nonreducing SDS-PAGE sample buffer and after 15 min the suspension was centrifuged in a Spin-X centrifuge tube filter (Costar, U.S.A.), retaining the liquid phase containing the precipitated material. Then, 1.5 µl of 14.2 M β-mercaptoethanol was added to the precipitated material.

Various publications are set forth herein, the contents of which are hereby incorporated by reference in their entireties.

I claim:

1. A method for detectably labeling with biotin a subset of a larger population of proteins comprising the following steps:

(i) contacting the larger population of proteins with an affinity element, attached to a solid phase element, which selectively binds to the subset of proteins, under conditions which permit binding of the affinity element to the subset of proteins to occur;

(ii) removing protein not bound to the solid phase element;

(iii) linking biotin to the subset of proteins bound to the solid phase element; and (iv) eluting the subset of proteins linked to biotin.

2. The method of claim 1, wherein the affinity element is an antibody.

3. The method of claim 2, wherein the antibody is a monoclonal antibody.

4. The method of claim 2, wherein the antibody is directed toward phosphotyrosine and the subset of proteins is phosphotyrosine-containing proteins.

5. The method of claim 2 wherein the antibody is a monoclonal antibody.

6. The method of claim 1, wherein the affinity element is a lectin and the subset of proteins is glycoproteins.

7. The method of claim 6 wherein the glycoproteins are selectively eluted using methyl α-D-mannopyranoside.

8. The method of claim 1, wherein the affinity element is a ligand for a receptor expressed on the subset of proteins.

9. The method of claim 1, wherein the affinity element is a substrate for an enzyme.

10. The method of claim 1, wherein the affinity element is a cofactor for an enzyme.

11. The method of claim 1 further comprising linking the biotin to the subset of proteins by contacting said subset with NHS-biotin.

12. The method of claim 11 wherein the NHS-biotin is at a concentration of about 3.2 percent (v/v) and the contacting occurs for 30 minutes.

* * * * *